(12) United States Patent
Schnell et al.

(10) Patent No.: US 11,345,875 B2
(45) Date of Patent: *May 31, 2022

(54) SYSTEMS AND METHODS FOR EXTRACTING OIL FROM PLANT MATERIAL

(71) Applicant: POET Research, Inc., Sioux Falls, SD (US)

(72) Inventors: Blake A. Schnell, Harrisburg, SD (US); Kristin M. Calar, Sioux Falls, SD (US); John C. Keeler, Sheboygan, WI (US); Matthew J. Rindsig, Harrisburg, SD (US); Benjamin G. Oster, Brandon, SD (US); Brett A. Flittie, Harrisburg, SD (US); Steven T. Bly, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/776,295

(22) Filed: Jan. 29, 2020

(65) Prior Publication Data

US 2020/0165540 A1 May 28, 2020

Related U.S. Application Data

(63) Continuation of application No. 16/101,256, filed on Aug. 10, 2018, now Pat. No. 10,584,304.

(Continued)

(51) Int. Cl.
*C11B 13/00* (2006.01)
*C12P 7/06* (2006.01)
(Continued)

(52) U.S. Cl.
CPC .............. *C11B 13/00* (2013.01); *C11B 7/005* (2013.01); *C12P 7/06* (2013.01); *C12P 7/64* (2013.01);
(Continued)

(58) Field of Classification Search
CPC . C11B 13/00; C11B 7/005; C11B 1/04; C12P 7/06; C12P 7/64
(Continued)

(56) References Cited

U.S. PATENT DOCUMENTS 7,608,729 B2 10/2009 Winsness et al.
7,842,484 B2 11/2010 Lewis
(Continued)

FOREIGN PATENT DOCUMENTS

WO    2014018479 A1    1/2014
WO    WO-2014018479  *  1/2014 ................ C12P 7/16
(Continued)

OTHER PUBLICATIONS

Savoire, et al. (2013) "Mechanical Continuous Oil Expression from Oilseeds: A Review", Food Bioprocess Technology 6:1-16.
(Continued)

*Primary Examiner* — Deborah D Carr
(74) *Attorney, Agent, or Firm* — Kagan Binder, PLLC

(57) ABSTRACT

Disclosed are methods and systems for recovering oil from processed plant materials and by-products formed during a milling process used for producing ethanol.

22 Claims, 11 Drawing Sheets

Related U.S. Application Data

(60) Provisional application No. 62/544,542, filed on Aug. 11, 2017.

(51) Int. Cl.
*C12P 7/64* (2006.01)
*C11B 7/00* (2006.01)
*C11B 1/04* (2006.01)

(52) U.S. Cl.
CPC ......... *C12Y 302/01001* (2013.01); *C11B 1/04* (2013.01)

(58) Field of Classification Search
USPC ....................................................... 554/175
See application file for complete search history.

(56) References Cited

U.S. PATENT DOCUMENTS

| | | |
|---|---|---|
| 7,919,291 B2 | 4/2011 | Lewis et al. |
| 8,192,627 B2 | 6/2012 | Gallop et al. |
| 8,449,728 B2 | 5/2013 | Redford |
| 8,454,802 B2 | 6/2013 | Redford |
| 8,603,786 B2 | 12/2013 | Redford |
| 8,702,819 B2 | 4/2014 | Bootsma |
| 8,722,911 B2 | 5/2014 | Bleyer |
| 9,051,538 B1 | 6/2015 | Roa-Espinosa |
| 9,061,987 B2 | 6/2015 | Bootsma |
| 9,139,803 B2 | 9/2015 | Redford |
| 9,388,475 B2 | 7/2016 | Lee |
| 9,394,505 B2 | 7/2016 | Sticklen et al. |
| 9,516,891 B1 | 12/2016 | Roa-Espinosa |
| 9,730,463 B1 | 8/2017 | Roa-Espinosa |
| 9,896,643 B2 | 2/2018 | Redford |
| 9,914,898 B2 | 3/2018 | Hakmiller |
| 9,914,899 B2 | 3/2018 | Bingeman et al. |
| 10,021,897 B2 | 7/2018 | Redford |
| RE47,268 E | 3/2019 | Roa-Espinosa |
| 10,584,304 B2 * | 3/2020 | Schnell ............... C11B 13/00 |
| 10,781,398 B2 | 9/2020 | Kreel et al. |
| 2010/0159549 A1 | 6/2010 | Redford |
| 2010/0159551 A1 | 6/2010 | Redford |
| 2013/0121891 A1 | 5/2013 | Dieker et al. |
| 2013/0164795 A1 | 6/2013 | Lowe et al. |
| 2014/0017728 A1 | 1/2014 | Bleyer et al. |
| 2014/0273127 A1 * | 9/2014 | Fuchs ....................... C12P 7/10 435/160 |
| 2015/0191750 A1 * | 7/2015 | Bleyer .................. C12P 5/023 435/71.1 |
| 2015/0201647 A1 | 7/2015 | Fosdick et al. |
| 2016/0152931 A1 | 6/2016 | Bootsma |
| 2018/0199591 A1 | 7/2018 | Kindelspire et al. |
| 2019/0119711 A1 | 4/2019 | Lee |

FOREIGN PATENT DOCUMENTS

| | | | |
|---|---|---|---|
| WO | 2015168020 A2 | 11/2015 | |
| WO | WO-2015168020 | * 11/2015 | ............... C12P 7/06 |
| WO | 2017059083 A1 | 4/2017 | |
| WO | WO-2017059083 | * 4/2017 | ............... C12P 7/64 |

OTHER PUBLICATIONS

Valicor, White Paper, (2015) "Back-End Value Enhanced through Patented Technology and Strategic Partnerships", Vital for Tommorow, www.valicor.com, Info@valicor.com, pp. 1-5.

Wang, H. et. al., (2008) "Effect of the Corn Breaking Method on Oil Distribution between Stillage Phases of Dry-Grind Corn Ethanol Production", Iowa State University, Digital Repository @ Iowa State University, Food Science and Human Nutrition Publication and Papers, J. Agric. Food Chem, 56(21), pp. 9975-9980.

Dickey, L. C., et al., (2009) "Foam Separation of Oil from Enzymatically Treated Wet-Milled Corn Germ Dispersions", J. Am Oil Chem Soc., 86, pp. 927-932.

Majoni, S. et. al., (2011) "Physical and Chemical Processes to Enhance Oil Recovery from Condensed Corn Distillers Solubles", J. Am Oil Chem Soc., 88, pp. 425-434.

Wang, T., "Maximizing Oil Recovery from Corn Fermentation By-products", Power Point Slides, Food Science and Human Nutrition, Iowa State University, Aug. 24, 2018 pp. 1-20.

Majoni, S. et. al., (2011) "Enzyme Treatments to Enhance Oil Recovery from Condensed Corn Distillers Solubles", J. Am Oil Chem Soc., 88, pp. 523-532.

Wang, H. et. al., (2009) "Effect of Low-Shear Extrusion on Corn Fermentation and Oil Partition", Iowa State University, Digital Repository, Food Science and Human Nutrition Publication, J. Agric. Food Chem, 57(6), pp. 2302-2307.

Fang, L. et al. (2015) "Synergistic effect of surfactants and silica nanoparticles on oilrecovery from condensed corn distillers solubles (CCDS)", Industrial Crops and Products, 77, 553-559.

Fang, L. et al. (2018) "Use of surfactant and enzymes in dry-grind corn ethanol fermentation improves yield of ethanol and distillers corn oil", Industrial Crops & Products, 111, 329-335.

Manjoni, S., (2010) "Characterization of Oil Precipitate and Oil Extracted from Condensed Corn Distillers Solubles", J Am Oil Chem Soc, 87, 205-213.

Sekhon, J.K., (2018) "Effect of co-products of enzyme-assisted aqueous extraction of soybeans,enzymes, and surfactant on oil recovery from integrated corn-soy fermentation", Industrial Crops & Products,121, 441-451.

Wang, H., (2010) "Effects of Kernel Breakage and Fermentation on Corn Germ Integrity and Oil Quality", Journal of Agricultural and Food Chemistry, 58, 10039-10044.

Wang, H., (2009) "A Laboratory Decanting Procedure to Simulate Whole Stillage Separation in Dry-Grind Corn Ethanol Process", Journal Am. Oil Chem. Soc., 10 pages.

"CoProMax™ Process, Bringing Additional Value and Efficiency to Ethanol Coproduct Production", retrieved from http://harvestingtech.com/wordpress/wp-content/uploads/copromax_presentation.pdf, (19 pages).

* cited by examiner

SYSTEMS AND METHODS FOR EXTRACTING OIL FROM PLANT MATERIAL

CROSS REFERENCE TO RELATED APPLICATIONS

This application is a continuation of U.S. application Ser. No. 16/101,256 filed Aug 10, 2018, which claims the benefit of U.S. Provisional Patent Application Ser. No. 62/544,542, filed Aug. 11, 2017, wherein the contents of the applications are each incorporated herein by reference in their entireties.

BACKGROUND

Plant material (e.g. cereal grains) is often used as feedstock for the production of target chemicals in a biorefinery. The plant material is typically milled and further processed to convert starch and/or fiber into fermentable sugars. The sugars are then converted by microorganisms, such as bacteria, yeast or both, in a fermentation process to produce a fermentation product. The fermentation product includes the target chemical and other materials which may include for example, water and other components such as oils, proteins, and residual carbohydrates including starches, sugars, and fiber. The target chemical is separated from the fermentation product and the other components are often collected as one or more co-products. A valuable class of co-products is oil.

The separation of oil from the fermentation product and other components is difficult because a portion of the oil remains bound or trapped in the other components such e.g. in the germ and fiber. What are needed are systems and methods that increase the release of bound or trapped oil in biorefinery process streams to facilitate oil separation and thereby increase oil yield. Obtaining additional oil from otherwise recalcitrant sources, particularly in ethanol production processes, are desirable to increase the overall value of the production process.

SUMMARY

Disclosed are methods and systems of extracting or releasing oil from processed plant materials.

In one aspect of the invention is disclosed a method of extracting oil from a processed plant material, wherein the method comprises:
 (a) providing a slurry comprising:
   i) processed plant material; and
   ii) an aqueous carrier, wherein the slurry comprises a total solids content in a range from 15 to less than 35% (wt/wt) based on the total weight of the slurry;
 (b) applying pressure to the slurry to move oil from the processed plant material to the aqueous carrier;
 (c) separating the slurry into a liquid fraction and a solid fraction; and
 (c) recovering or separating oil from the liquid fraction.

In another aspect of the invention is a system for extracting oil from a processed plant material, wherein the system comprises:
 a) a source of a slurry comprising:
   i) processed plant material; and
   ii) an aqueous carrier, wherein the slurry comprises a total solids content in a range from 15 to less than 35% (wt/wt) based on the total weight of the slurry;
 b) an oil liberation system in fluid communication with the source of the slurry, wherein the oil liberation system is configured to (adapted to) apply pressure to the slurry to move oil from the processed plant material to the aqueous carrier;
 c) a solid liquid separation system configured to separate the slurry into a liquid fraction and a solid fraction; and
 d) an oil recovery or separation system in fluid communication with the solid liquid separation system to receive the liquid fraction, wherein the oil recovery or separation system is configured to recover or separate oil from the liquid fraction.

In yet another aspect of the invention is a method of extracting oil from a processed plant material, wherein the method comprises:
 (a) providing a slurry comprising:
   i) processed plant material; and
   ii) an aqueous carrier, wherein the slurry comprises a total solids content in a range from 15 to less than 35% (wt/wt) based on the total weight of the slurry, wherein providing the slurry comprises screening the processed plant material to separate the slurry into a first liquid fraction and a first solid fraction; and
 (b) pressing the first solid fraction to separate the first solid fraction into a second liquid fraction and a second solid fraction and to move oil into the second liquid fraction; and
 (c) recovering or separating oil from the second liquid fraction.

The disclosed method and system aid in releasing or liberating bound or trapped oil making it available for further extraction and processing.

BRIEF DESCRIPTION OF THE DRAWINGS

Various examples of the present disclosure will be discussed with reference to the appended drawings. These drawings depict only illustrative examples of the invention and are not to be considered limiting of its scope.

DESCRIPTION

Disclosed in embodiments herein are methods and related systems for liberating oil from processed plant materials in a biorefinery process stream. Liberation of oil means releasing oil from materials in a process stream such that the oil may be further processed such as for example separating the oil from the process stream. Oil may be physically or chemically bound with plant components (e.g. fiber, protein, carbohydrates) and subsequent processes may benefit from methods and systems that work to free the oil from those components. An input stream that is treated by methods and systems according to the present disclosure may be in the form of a slurry. The slurry may include an aqueous carrier and a total solids content. Such a slurry can facilitate liberating oil from a plant material that otherwise can be relatively difficult to liberate without e.g. using large quantities of organic solvents such as e.g. hexane extraction.

In embodiments, the plant material is a cereal grain that is processed to form a biochemical such as e.g. ethanol. In an embodiment, raw material containing starch may be milled to open up the structure and allow for further processing. Dry milling as well as wet milling may be used. When wet milling is applied, the steps of soaking or steeping may precede milling. Methods for producing alcohol during fermentation are disclosed in U.S. Pat. Nos. 7,842,484 and 7,919,291 and are hereby incorporated by reference in their entireties.

As used herein, the term "slurry" refers to a fluid that includes processed plant material and a liquid aqueous carrier. The processed plant material can include solids that become dissolved in the aqueous carrier as well as undissolved solids mixed with the aqueous carrier.

As used herein, the term "aqueous carrier" may include to fresh water, recycled process water, thin stillage, alcohol, or combinations thereof.

As used herein, the term "fermentation" refers broadly to the enzymatic and anaerobic breakdown of organic substances by microorganisms to produce fermentation products. While fermentation generally occurs under anaerobic conditions it is not intended that the term be solely limited to strict anaerobic conditions, as fermentation may also occur in the presence of oxygen.

As used herein, the term "fermentation beer" or "beer" refers to the components after fermentation but before distillation.

As used herein, the term "stillage composition" refers to the components obtained after fermentation and distillation. The stillage composition encompasses whole stillage, thin stillage, wet cake and/or syrup.

Figure 1:
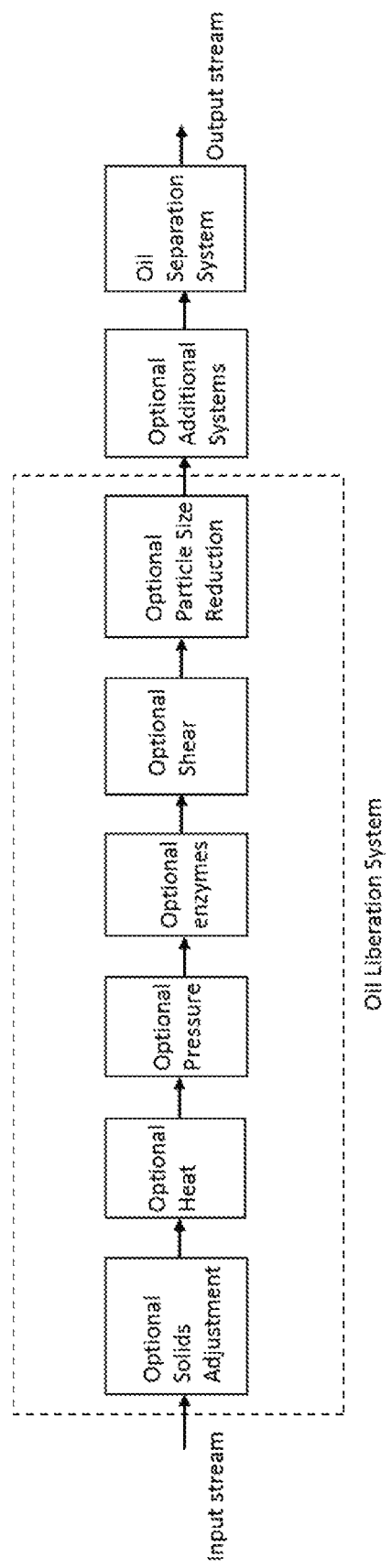
FIG. 1 is a block flow diagram of a system including an oil liberation system and an oil separation system.

FIG. 1 depicts an illustrative example of a system for treating an input stream including an oil liberation system to liberate oil from processed plant material and an oil separation system for separating the liberated oil from the stream. The system may include optional additional systems depending on the input stream.

The oil liberation system may optionally include systems and methods for adjusting solids content, heating, pressurizing, enzymatically treating, shearing, and reducing particle size. The liberated oil may be further separated. The oil separation system may include a variety of systems and methods for separating oil from a process stream. For example, oil separation and recovery may be carried out according to the methods and systems disclosed in U.S. Pat. Nos. 8,702,819, 9,061,987, 9,139,803, and 9,896,643, PCT International Application Publication No. WO 2017/059083, and US Patent Application 2016/0152931, all of which are hereby incorporated by reference in their entireties for all purposes. Additional optional systems may include distillation, decanting, evaporating, and/or drying. It should be understood that the order in which the method and system is carried out can vary and FIG. 1 is only an illustration of one such method.

The input stream into the system can be provided from a variety of processed plant materials. Non-limiting examples of processed plant material include milled grain. In some embodiments, milled grain includes wet-milled grain and/or dry-milled grain. Non-limiting examples of grain include corn, soybean, sorghum, wheat, rice, barley, oats, millet, rye, or any other grains that are capable of being fermented. In some embodiments, dry-milled grain includes whole ground corn.

A slurry according to the present disclosure can be generated from a variety of processed plant materials. Non-limiting examples of a slurry include grain mash, fermentation beer, whole stillage, wet cake, and combinations thereof. One or more of these slurries are present, e.g., in a corn ethanol process that includes grinding, mashing, fermenting, and distilling systems and methods.

Depending on the slurry to be inputted into the system, the amount of solids in the slurry may be adjusted by a variety of ways to facilitate oil liberation. Without being bound by theory, it is believed that having an appropriate amount of aqueous carrier in the slurry aids in transport of the oil adsorbed on and/or entrained in the processed plant material out of such material and into the aqueous carrier from whence it can be subsequently separated. Without being bound by theory, it is also believed that having an appropriate amount of aqueous carrier in the slurry which includes less oil than is bound with the solids results in an oil concentration gradient between the solids and the carrier that promotes release of oil from the solids and into the aqueous carrier.

The solids content of the slurry can be decreased by e.g. adding water and/or ethanol to the slurry. The solids content of the slurry can be increased by e.g. using a settling tank, screening or filtering the slurry, evaporating the slurry, and/or centrifuging the slurry e.g. with a decanter, disc stack, and/or hydroclone.

In embodiments, a solid fraction (e.g. a cake fraction) can be diluted with liquid to result in the desired solids concentration. In embodiments, the liquid is water, alcohol, thin stillage, process water or combinations thereof.

In embodiments, the desired solids concentration can be directly obtained from an existing process by adjusting a solid liquid separation step, e.g. decanting, to produce an appropriate stream, e.g. wet cake with a lower than typical solids content.

In embodiments, the solids content of a process stream is adjusted by a screen that removes fine solids (for example in a wet cake). In embodiments, the screen has openings or pore sizes from 750 micrometers, 500 micrometers, or 250 micrometers. In embodiments, the gravity screen has openings or pore sizes from 750 micrometers, 500 micrometers, or 250 micrometers.

In some embodiments, a slurry includes total solids in a range from 15 to less than 35%, from 15 to 30%, from 17 to 25%, or even about 20% (wt/wt) based on the total weight of the slurry. As used herein, "total solids" includes dissolved and undissolved solids. In embodiments, the slurry can be beer or whole stillage. In embodiments, the beer or whole stillage contains from about 0.5 wt % to 3% wt fat based on the total beer or whole stillage, from about 0.5 wt % to 1 wt %, from 1 wt % to 2 wt %, or from 1.5 wt % to 2.5 wt % fat based on the total beer or whole stillage. In embodiments, a slurry may itself undergo further processing to result in a slurry that will further be adjusted to the appropriate solids content as described herein.

In some embodiments, the aqueous carrier comprises at least 50 percent water based on the total volume of the carrier, at least 60 percent water based on the total volume of the carrier, at least 70 percent water based on the total volume of the carrier, at least 80 percent water based on the total volume of the carrier, or even at least 90 percent water based on the total volume of the carrier. In some embodiments, the aqueous carrier includes less than 10 percent, less than 5 percent, less than 1 percent, or even less than 0.5 percent of organic solvent based on the total volume of the carrier.

In some embodiments, the aqueous carrier does not include exogenous (added) organic solvent. Advantageously, organic solvents can be avoided if desired. Non-limiting examples of such organic solvents include hexane, ethyl esters, ethanol, combinations thereof, and the like. When a solvent is used, it is advantageous to use a solvent that is produced in the biorefinery in which oil liberation is performed. For example, in a grain-to-ethanol biorefinery, it is advantageous to use ethanol which is produced in the biorefinery and which may be subsequently recovered in normal process steps.

After the slurry is adjusted to the appropriate solids content, the slurry may be subjected to processes that aid in disrupting and further releasing the oil from the rest of the materials. Disruption and separation may be achieved by any suitable manner such as by imparting sheer pressure, compression, or both. In embodiments, the slurry may be mixed or agitated (via a paddle mixer), can be spun (e.g. in a centrifuge (e.g. decanter or disc-type)), or pressed (e.g. in a screw press). In embodiments, the slurry may be subjected to one or more disc mills (e.g. single or double disc mills), hammer mills, or colloid mills.

One or more parameters can be selected to facilitate a desired oil yield. Non-limiting examples of such parameters such as for a screw press include screen size, screw speed, backpressure, liquid injection and screw design and configuration. In embodiments, the slurry may be processed by reducing the particle size. In embodiments, particle size may be reduced by a colloid mill. The particle size distribution of a whole stillage stream may have a peak around approximately 500 microns. Reducing the average particle diameter (size) of a slurry composition increases the overall particle surface area and reduces the distance though which a bound oil droplet must travel to exit a particle and enter the liquid phase of the slurry. Both of these phenomena conceivably aid in the release of bound corn oil.

In embodiments, the slurry or streams may be subjected to heating. Any suitable method of heating can be used, such as for example, via direct steam injection or by heat exchangers. In embodiments, the heat exchanger has tube heat exchanger elements. The slurry is heated from ambient temperature to approximately 21.1° C. (70° F.) to 98.8° C. (210° F.); from 21.1° C. (70° F.) to 65.5° C. (150° F.); from 60° C. (140° F.) to 65.5° C. (150° F.); from 60° C. (140° F.) to 98.8° C. (210° F.); or from 21° C. (70 ° F.) to about 100° C. (212° F.).

Without being bound by theory, it is believed that increasing the temperature of the stream reduces the viscosity of the oil or otherwise makes it more amenable to transport out of the plant material and into the aqueous carrier. In addition to heat exchangers and direct heat injection, heating may be accomplished, e.g., by friction (e.g. pressing, shearing, pumping).

In embodiments, the slurry or streams may be subjected to pressure above ambient pressure. In embodiments, pressure is 20-600 psi, 20-100 psi, 100-300 psi, 200-400 psi, or 300-600 psi. Without being bound by theory, the high pressure causes extraction of the protein fraction via a selective solubilization, which disrupts the solid matrix of the processed plant materials in the slurry allowing release of bound or trapped oil. In embodiments, a high shear force and a high pressure are used, which is characterized by successive pressure/cavitation cycles.

Pressure may be imparted to the process stream by pumping, pressing, milling, and other pressure processes. In embodiments, the pressure is achieved by pumping the slurry into a reactor designed with narrow tubes that achieve a pressure drop across the tube side. In an embodiment, the process stream is pressurized by pumping it into a shell and tube heat exchanger with the pump increasing the fluid pressure in opposition to the flow restriction caused by the heat exchanger. In embodiments, the process stream is pressurized by pressing it in a screw press, disc mill, colloid mill and the like. In embodiments, the process stream is allowed to rapidly expand after compression to facilitate oil transport. Such expansion may further disrupt the structure of the plant material to further facilitate oil transport.

Enzymes may be added to one or more process streams to break down the plant material and facilitate oil transport out of the plant material. In embodiments, fermentation beer or stillage compositions can be treated with one or more enzymes to facilitate breakdown of the undissolved solids to help release oil. In embodiments, the whole stillage can be treated with one or more enzymes to facilitate breakdown of the undissolved solids to help release oil. For example, the one or more enzymes could target, e.g., residual starch (amylase), cellulose (cellulase), hemicellulose (hemicellulase), and/or protein (protease). If the stillage composition is at a high temperature, it can be advantageous to use a high temperature enzyme. For example, a high temperature alpha amylase, such as Fuelzyme can be used to treat whole stillage prior to centrifuging to improve oil extraction. Without being bound by theory, it is believed that the alpha amylase can reduce viscosity by deconstructing starch to smaller glucose polymers and cellulase can help release entrained oil. Similarly, it is believed, e.g., that a cellulase, hemicellulase, and/or protease can break down the structure of the solids to aid in releasing oil. The combination of enzymatic treatment of stillage compositions and shearing of the stillage complement one another. Shear can be applied after enzymatic treatment. For example, the treated stillage composition can be mixed, e.g. with a paddle mixer. In another example, the treated stillage can be spun, e.g. in a centrifuge. In another example, the treated stillage can be pressed, e.g. in a screw press.

Shear may be imparted to the process stream by pumping, pressing, milling, and other shearing processes. In embodiments, the process stream is sheared by processing it in a screw press, disc mill, colloid mill and the like.

The size of solid particles may be reduced by pumping, pressing, milling, and other shearing processes. In embodiments, particles in the process stream are reduced by processing the stream in a screw press, disc mill, colloid mill and the like.

Figure 2:
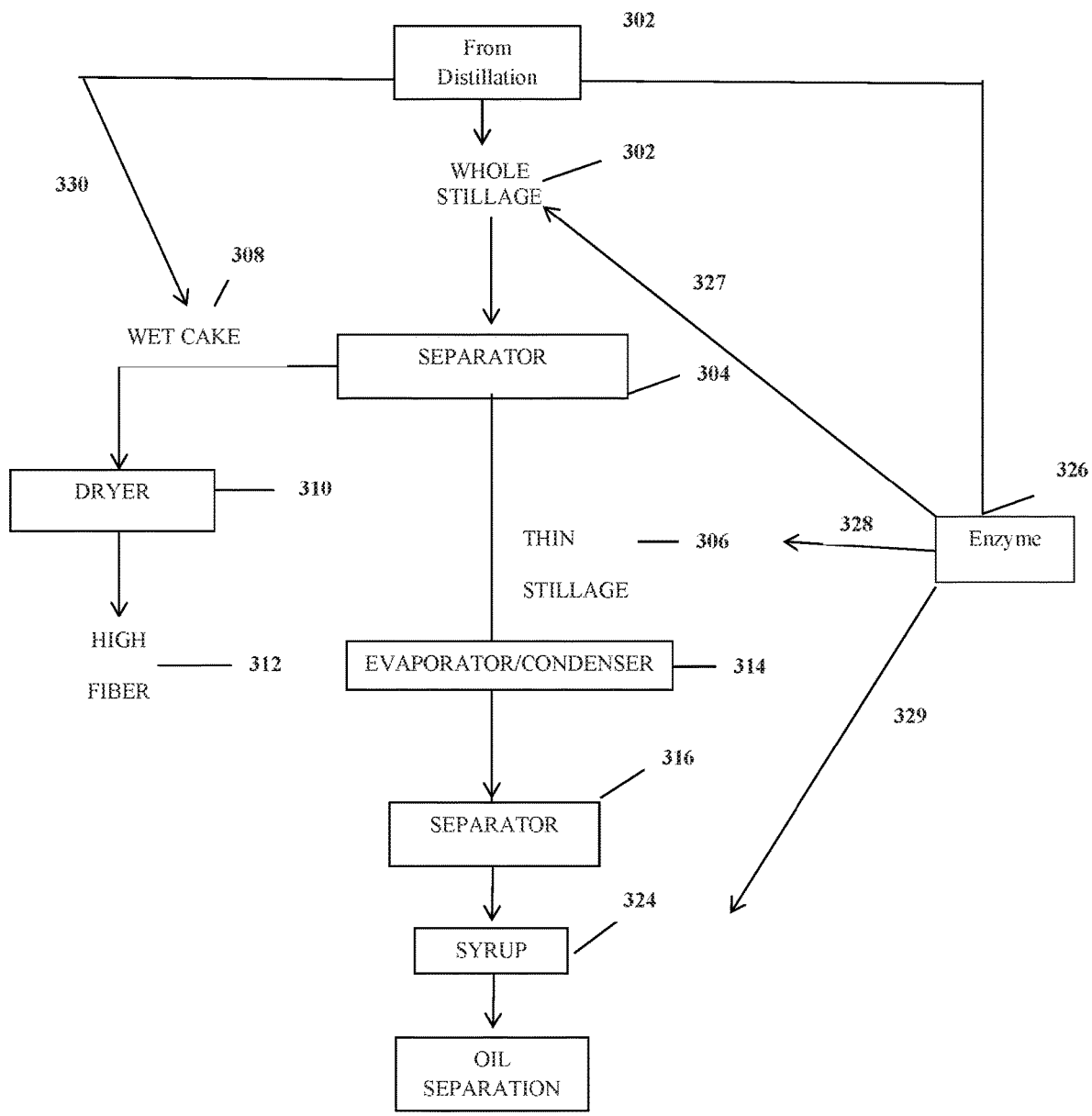
FIG. 2 is a block flow diagram illustrating an embodiment of a system for fractionating whole stillage and subsequent oil separation.

The illustrative example of FIG. 2 depicts a system for fractionation of whole stillage. As noted above, a stillage composition refers to the components obtained after fermentation and distillation. The stillage composition can be typically obtained from fermentation processes by first grinding sugar-containing materials (e.g. starch containing materials) in a dry-grind or wet-milling process, then breaking down or saccharifying the material into sugars using enzymes, and finally converting the sugars directly or indirectly into a desired product. In the illustrative example of FIG. 2, a grain mash such as corn mash has been fermented with yeast to produce ethanol. The fermentation product or beer can include ethanol, water, oil, additional soluble components, unfermented particulate matter, residual fibers and polysaccharides, and the like. The beer can then be distilled to provide ethanol, leaving the remaining components as "whole stillage." The whole stillage may be further separated to provide a liquid component, referred to as "thin stillage" and a solid component, referred to as "wet cake" or "wet grains."

In the illustrative example of FIG. 2, the whole stillage 302 is provided to a stillage separator 304 for separation of the stillage into a solids component (e.g. wet cake) and a liquid component (e.g. thin stillage) 306. The separation may be performed with a screw press, centrifuge (e.g. decanter, disc stack, screen bowl, hydroclone) or via screening or filtering type methodologies. One of ordinary skill in the art will appreciate that the speed or amount of centrifugal force applied will depend on various factors such as sample size and may be adjusted appropriately depending on such factors.

The solid component or wet cake 308 contains a high solids content, which may be dried at a dryer 310 to a high fiber dried distillers grain (DDG) 312 product. In some embodiments, the wet cake may additionally undergo a washing step prior to being dried. The wash fluid may be combined with the liquid thin stillage, in some embodiments. Separation of the solid component from the thin stillage may be performed soon after initial production of the stillage.

The resulting liquid thin stillage 306 is provided to an evaporator 314 or a series of evaporators to condense the thin stillage to syrup 324, or may be recycled back into the system or into a tank as "backset". The syrup may be blended into DDG or added to the wet cake before drying to produce "Distillers Dried Grain with Solubles" (DDGS).

One or more enzymes can be added at one or more points of processing and production of stillage composition to further breakdown the processed plant material the solids structure to aid in liberating oil. In the illustrative example of FIG. 2, one or more enzymes 326 may be added to whole stillage 327, thin stillage 328, syrup 329 or wet cake 330. Without being bound by theory, it is believed that the enzymatic breakdown of the processed plant material structure facilitates the liberation of oil from the processed plant material. Oil may be separated from the one or more process streams using an oil separation system.

Figure 3:
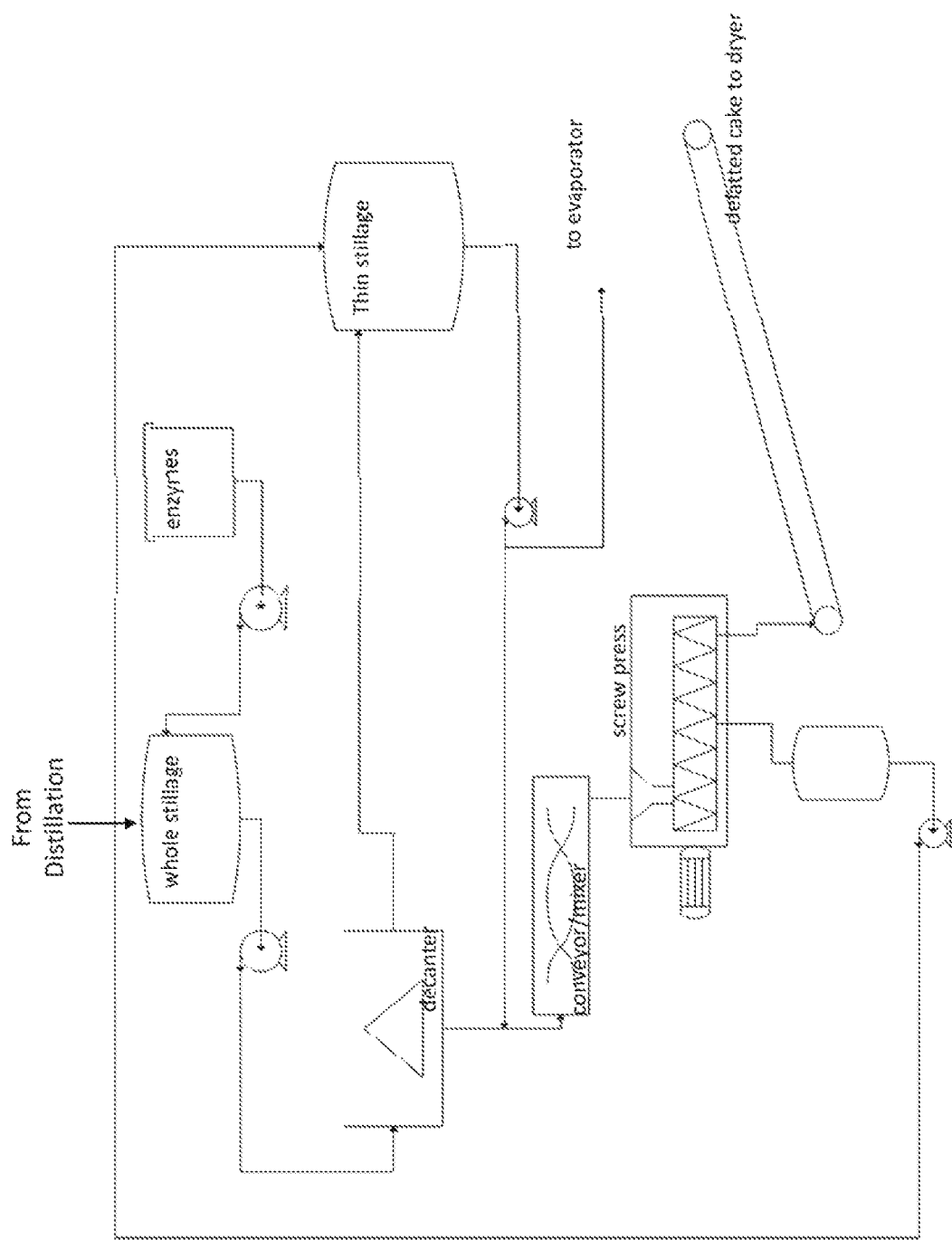
FIG. 3 is a schematic diagram illustrating an embodiment of a screw press oil liberation process flow.

In the illustrative example of FIG. 3, a solid/liquid separator (e.g. a gravity screen or decanter centrifuge) is configured to separate an input stream of processed plant material into a solid fraction and a liquid fraction, where the liquid fraction passes through the screen. The input stream may be fermentation beer or whole stillage. In the illustrative example of FIG. 3, whole stillage is separated into thin stillage (the liquid fraction) and wet cake (the solid fraction) so that the wet cake includes a total solids content of 35% (wt/wt) or greater based on the total weight of the wet cake, followed by diluting the wet cake (e.g., with thin stillage) so that the wet cake includes total solids in a range from 15 to less than 35% (wt/wt) based on the total weight of the wet cake. Diluting a slurry such as wet cake can be performed with an aqueous composition that is similar to or the same in composition as the aqueous carrier of the slurry as described above. In some embodiments, an aqueous composition used for diluting the slurry (e.g., wet cake) includes process water, ethanol, thin stillage, or combinations thereof.

Alternatively, the solid/liquid separator, i.e., decanter (optionally a gravity screen) can be configured to separate whole stillage into thin stillage and wet cake so that the wet cake formed directly from whole stillage has a total solids in a range from 15 to less than 35% (wt/wt) based on the total weight of the wet cake and no dilution is necessary.

In the illustrative example of FIG. 3, one or more decanter centrifuges (connected in series or parallel) can separate whole stillage into a wet cake stream and a thin stillage stream (the decanter liquid stream, which can also be referred to as "centrate"). Wet cake, e.g., can include a significant amount of oil, approximately 40% of the total oil in the corn, which is absorbed on or entrained in the wet cake stream. In some embodiments, this equates to an amount less than about 6% wt/wt oil in the wet cake. In some embodiments, at least a portion of this oil in the wet cake can be recovered by diluting the wet cake as shown in FIG. 3 with thin stillage to about 20% total solids and pressing the diluted wet cake with a screw press to form a press liquor that includes corn oil. Without being bound by theory, it is believed that the extra water present in the wet cake due to dilution with thin stillage aids in transport of the oil adsorbed on and/or entrained in the wet cake out of the wet cake and into the thin stillage during pressing. This can increase the amount of oil available in the thin stillage and can result in increased oil yield.

The press liquid from the screw press, with the additional oil liberated during pressing, is combined with the thin stillage in a thin stillage tank. A portion of the oil laden thin stillage is sent to an evaporator where it is concentrated into an oil bearing syrup from which the oil is subsequently separated. The defatted wet cake is sent to a dryer to be dried to distillers dried grains. The defatted syrup, i.e. after oil separation, may be sent to the dryer with the wet cake to form distillers dried grains with solubles.

A particle size reduction step may be included at the whole stillage stream feeding the decanter, at the decanter cake stream leaving the decanter, at the conveyor/mixer feed stream, or at a combination of these locations. One advantage of reducing particle size at the conveyor/mixer feed stream is that the properties of this stream can be adjusted by adjusting the flow rate of the thin stillage stream that combines with the wet cake stream. In this way, plugging and bridging of material may be avoided. The particle size reduction step may comprise one or more disc mills, colloid mills, or other suitable equipment that is effective in reducing the particle size of the streams shown in FIG. 3. The particle size reduction step may comprise a combination of the aforementioned milling equipment.

Figure 4:
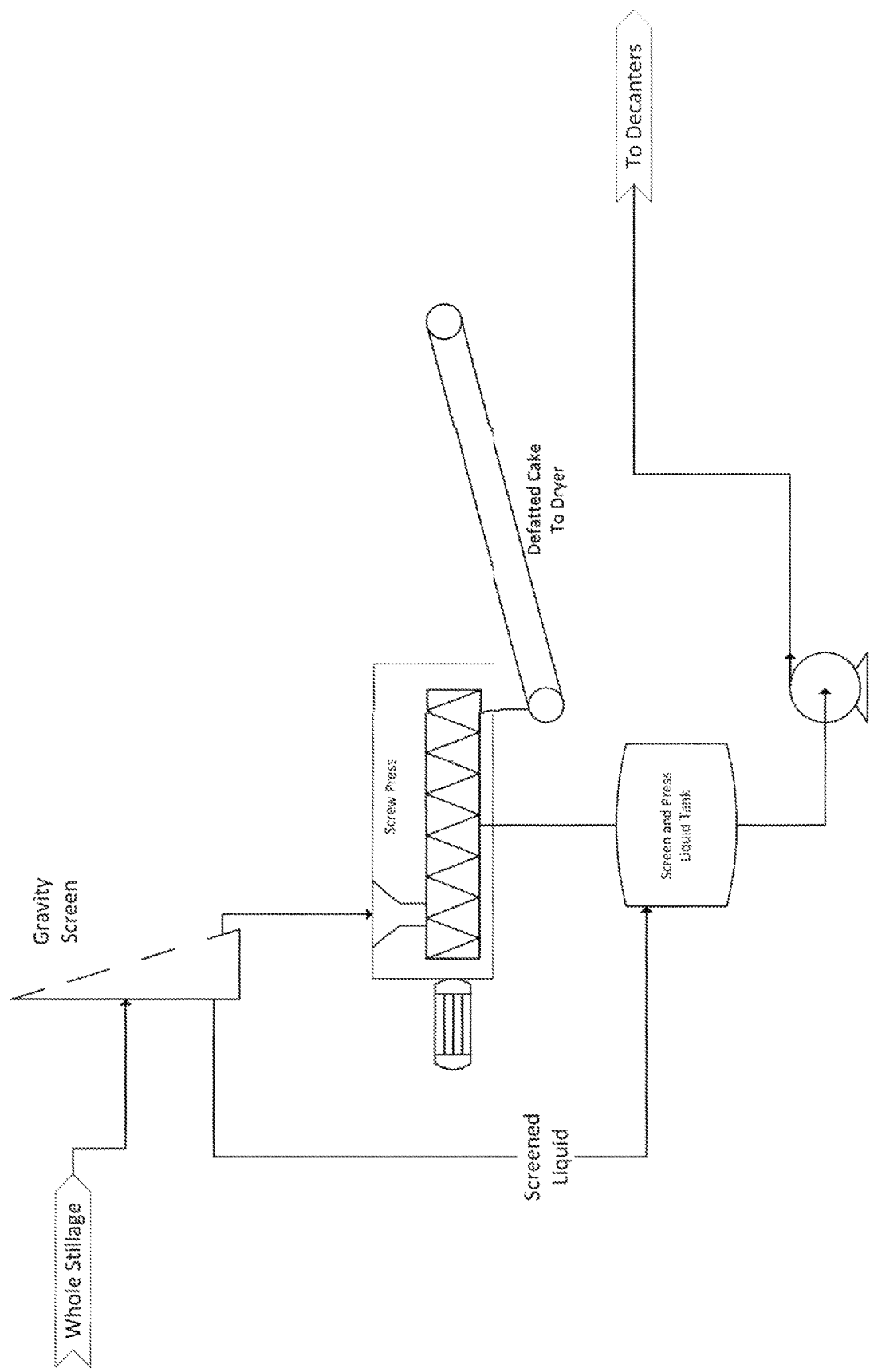
FIG. 4 is a schematic diagram illustrating an embodiment of a screw press oil liberation process flow with whole stillage prepared by gravity screening.

In the illustrative example of FIG. 4, whole stillage is processed with a gravity screen to directly produce a slurry ("screen overs") in a desired total solids range as described above. Using a gravity screen sized appropriately, fine solids can be removed from the wet cake (the fine solids can pass through the screen with excess liquid (liquid fraction)). Removal of fine solids from the material to be pressed can facilitate subsequent pressing in a screw press since it reduces or prevents blinding of the screw press screen by the fine solids. In the illustrative example of FIG. 4, the screen overs (solid fraction) are sent directly to the screw press for oil extraction/dewatering to produce a defatted cake and liquid. The defatted cake can be sold as wet cake and/or sent on to one or more dryers (not shown) to produce distillers dried grains or distillers dried grains with solubles. An optional particle size reduction step may be included to reduce the particle size of the whole stillage stream or the gravity screen overs. Optionally, a particle size reduction step may be included in both locations. The particle size reduction step may comprise one or more disc mills, colloid mills, or other suitable equipment that is effective in reducing the particle size of the streams shown in FIG. 4. The particle size reduction step may comprise a combination of the aforementioned milling equipment. A benefit of adding particle size reduction prior to the gravity screen is that all of the solids are treated. A benefit of adding particle size reduction after the gravity screen is that less equipment is required due to the lower flow rate of gravity screen overs (compared to the entire stream that feeds the gravity screen).

Figure 5:
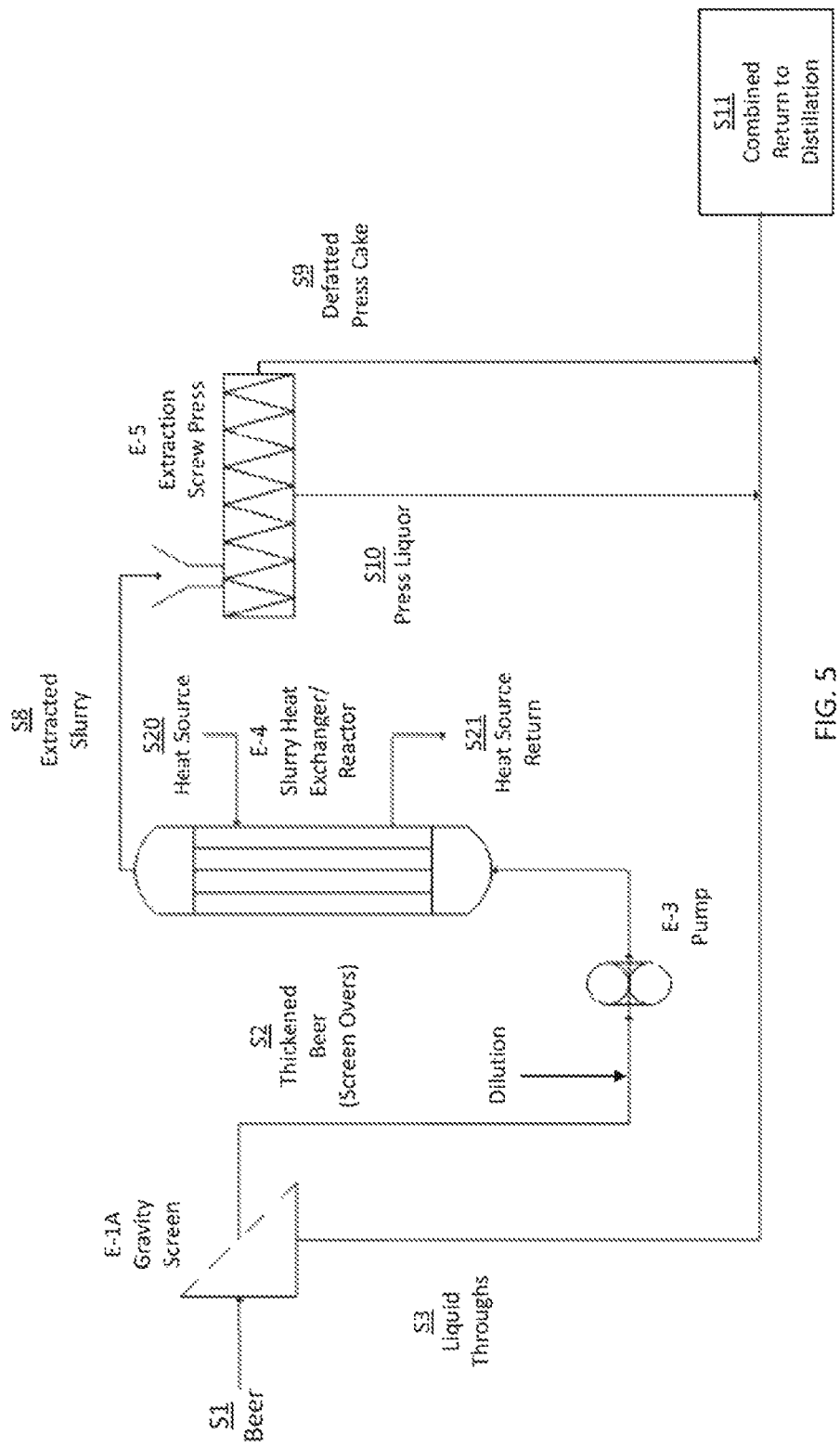
FIG. 5 is a schematic diagram illustrating an embodiment of a screw press oil liberation process flow with beer prepared with a gravity screen and a heat exchanger/reactor.

In the illustrative example of FIG. 5, beer or whole stillage is processed with a solid/liquid separator such as a gravity screen to directly produce a slurry ("screen overs") in a desired total solids range as described above. Using a gravity screen sized appropriately, fine solids are removed from the beer (the fine solids can pass through the screen with excess liquid (the liquid throughs). In the illustrative example of FIG. 5, the screen overs are adjusted to a pumpable slurry by dilution with the addition of alcohol (e.g. ethanol).

In embodiments, the alcohol is recycled 190 or 190 proof diluted) to a target ethanol concentration. In embodiments, the alcohol is 190 proof ethanol, 200 proof ethanol, aqueous ethanol (40%-92% ethanol, w/w), or any other solvent capable of extracting oil and/or protein (e.g. zein) from mash. In embodiments, the target alcohol amount is 0-95% w/w alcohol concentration or 40-70%, 50-90%, or 60-95% w/w alcohol concentration.

Other aqueous process streams may also be used to prepare a pumpable slurry. Non-limiting examples include: processed liquid, thin stillage, distillate, side stripper bottoms, liquid throughs (stream S3) or combinations thereof. Optionally, the process in FIG. 5 may be practiced without the addition of an alcohol or other liquid.

In the illustrative example of FIG. 5, the slurry is pumped with high pressure (e.g. 200-400 psi) through a heat exchanger/reactor designed with narrow tubes and a high pressure drop across the tube side. The slurry is heated up rapidly (within 5-20 seconds) from ambient temperature to approximately 65.5° C. (150° F.) using plug flow with minimal back-mixing, generating an extracted slurry. The rapid temperature increase, high pressure, and ethanol concentration combine to cause extraction of a protein fraction via selective solubilization, which disrupts the solids matrix and allows access to the trapped and bound oil fractions.

The extracted slurry is mechanically separated in a device (e.g. screw press) that imparts shear and compression to the slurry. This separation step produces a press liquor stream (S10) containing the additional oil, solubilized protein, and a majority of the aqueous ethanol; and a defatted cake stream containing the residual suspended solids and a small fraction of the aqueous ethanol (S9).

All product streams (S3, S10, S9) are recombined (S11), causing the extracted protein fraction to precipitate out of solution but the released oil remains liberated from the suspended solids. The combined stream is fed to distillation and subsequent oil separation.

An optional particle size reduction step may be included to reduce the particle size of the slurry stream or the gravity screen as in the previous examples.

Figure 6:
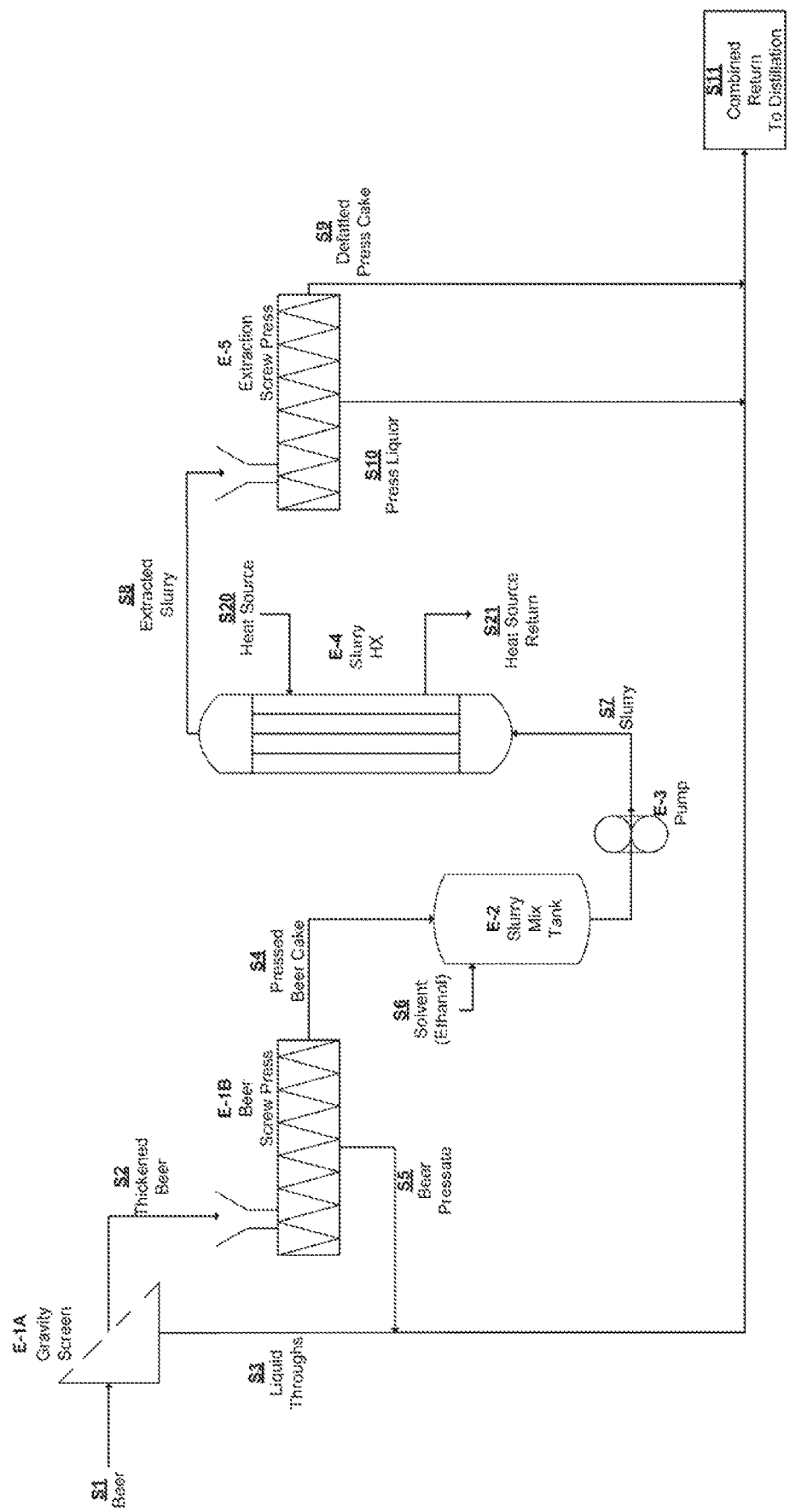
FIG. 6 is a schematic diagram illustrating an embodiment of a screw press oil liberation process flow with beer prepared with a gravity screen and a heat exchanger/reactor.

The illustrative example of FIG. 6, is similar to that of FIG. 5. In the illustrative example of FIG. 6, after the solid/liquid separation of beer or whole stillage via the gravity screen and before introduction into the heat exchanger/reactor, the screen overs are further pressed via a screw press. In the illustrative example of FIG. 6, the pressed beer cake can be held and diluted in a slurry mix tank before being introduced into the heat exchanger/reactor to be subjected to a high temperature, pressure or both. The pressed beer cake may be diluted to a pumpable slurry with alcohol or another liquid (e.g. processed liquid, thin stillage, distillate, side stripper bottoms, or combinations thereof).

As in the prior examples, an optional particle size reduction step may be included to reduce the particle size of the slurry stream or the gravity screen overs (S2). Optionally, a particle size reduction step may be included in both locations.

Figure 11:
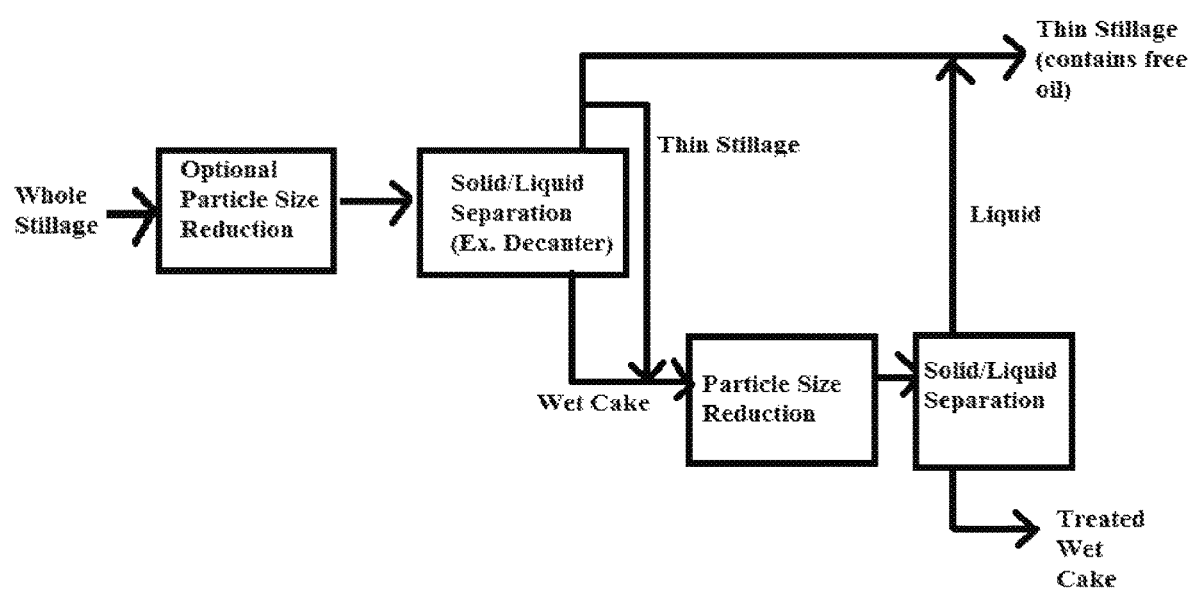
FIG. 11 is a block flow diagram illustrating optional particle size reduction to further increase oil liberation

FIG. 11 illustrates an illustrative particle size reduction arrangement that may be used in the examples of FIGS. 1-6. In the illustrative example of FIG. 11, a whole stillage stream is subjected to a particle size reduction step to free bound oil. The particle size reduction step may comprise one or more disc mills, colloid mills, or other suitable equipment that is effective in reducing the particle size of a whole stillage stream. Reducing particle size in the whole stillage stream is advantageous because all of the particles in the whole stillage are present for size reduction and potential oil release. After the whole stillage is subjected to a particle size reduction step, the size reduced whole stillage is separated in a solid/liquid separation step. The solid/liquid separation step may comprise one or more decanters (decanting centrifuges), one or more screw presses, or combinations thereof. The solid/liquid separation step separates a whole stillage stream (with reduced particle size) into a wet cake stream and a thin stillage stream. The thin stillage stream contains free oil that may subsequently be separated and recovered.

Optionally, the wet cake is subjected to a second particle size reduction step and a second solid/liquid separation step. The solid/liquid separation step may comprise one or more screw presses or decanters (decanting centrifuges) or combinations thereof. The optional second particle size reduction of the wet cake stream frees additional bound oil. The liquid stream from the second solid/liquid separation includes the free corn oil and may be recombined with the thin stillage for subsequent oil separation. Optionally, the first particle size reduction may be omitted an only the wet cake be subjected to particle size reduction. Subjecting just the wet cake to particle size reduction is advantageous because the flow rate of this stream is lower than the whole stillage stream or the fermentation beer stream. Therefore, the amount of equipment required to treat this stream is less, compared to treating streams with larger flow rates.

Optionally, a thin stillage dilution stream present may be separated from the thin stillage stream from the first solid/liquid separation step and combined with the wet cake to increase the moisture content of the wet cake stream, thereby making the diluted wet cake stream more flowable. This dilution stream is advantageous because it allows the wet cake stream's solids content and viscosity to be easily varied to optimize flow characteristics (e.g. to prevent plugging and/or bridging) and to achieve optimal particle size reduction in the particle size reduction step. A method of extracting corn oil from a stillage stream includes (a) providing a stillage stream, reducing the particle size of the stillage stream to form a treated stillage stream, separating the treated stillage stream into a liquid stream and a wet cake stream, and separating corn oil from the liquid stream. In embodiments the stillage stream is whole stillage or wet cake or both.

The present application is further illustrated in the following non-limiting examples. It will be recognized that various modifications and changes may be made to the experimental embodiments described herein, and without departing from the scope of the claims.

EXAMPLE 1

Whole stillage was treated with a high temperature (thermostable) alpha amylase enzyme (Fuelzyme produced by BASF) and separated into wet cake and thin stillage. The wet cake was diluted with thin stillage to a total solids content of 20% and pressed in a Vincent VP-4 screw press.

Figure 7:
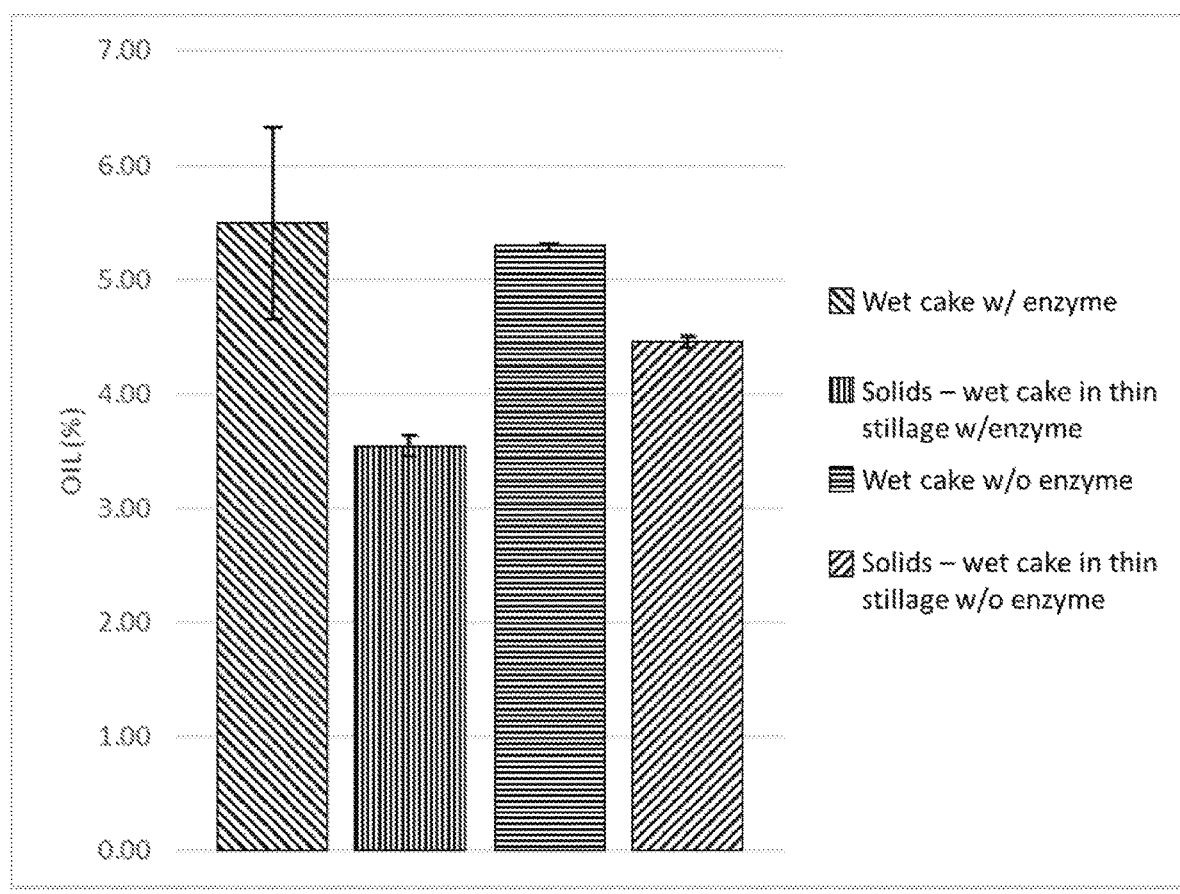
FIG. 7 is a graphical representation of oil remaining in solids after pressing compared to starting wet cake.

The wet cake resulting from whole stillage treated with Fuelzyme and wet cake resulting from whole stillage not treated with the enzyme had similar oil contents of 5.49% (left diagonally-lined column) and 5.29% (horizontal lined column), respectively, as shown in FIG. 7. Screw pressing the wet cake from whole stillage with Fuelzyme treatment resulted in solids ("defatted cake") with 3.54% (vertical lined column) oil content, which is a 35.5% reduction in oil. This is significant, even considering the large standard deviation exhibited by wet cake oil content from whole stillage with Fuelzyme treatment. Pressing the wet cake from whole stillage without Fuelzyme treatment resulted in solids ("defatted cake") containing 4.46% (right diagonally-lined column) oil for a 15.7% oil content reduction.

Figure 8:
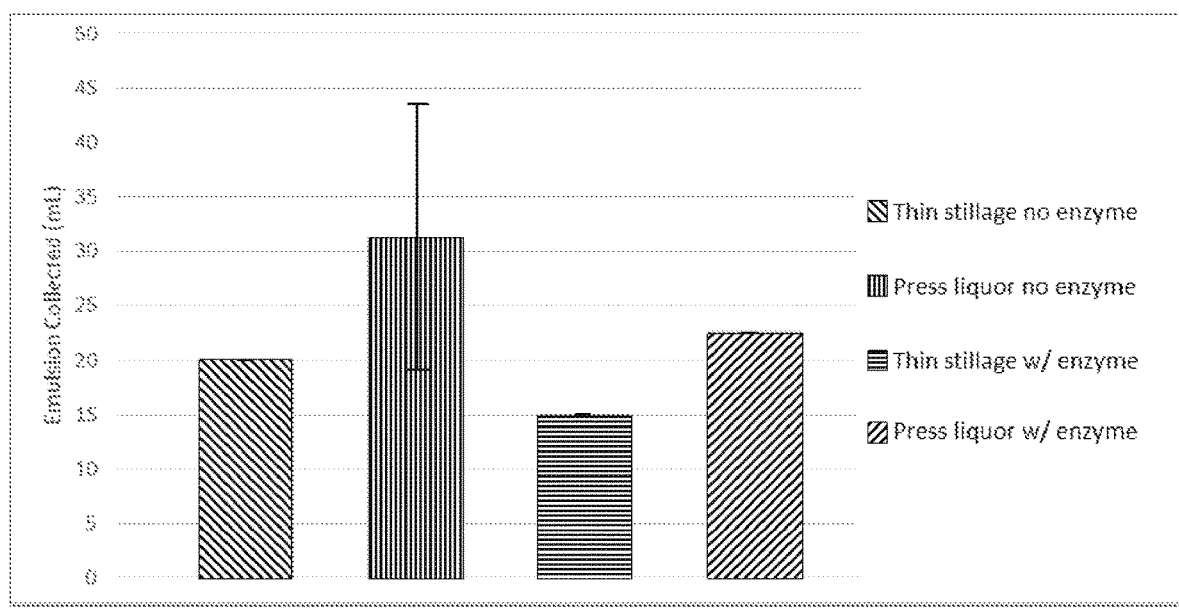
FIG. 8 is a graphical representation of screw press liquor spin test results.

As shown in FIG. 8, the oil content of the press liquor formed in the screw press agreed directionally with the wet cake oil results; although this metric indicated that more oil was pressed from the wet cake from whole stillage that had not been treated with Fuelzyme. The thin stillage used to dilute the screw press feed contained oil that should be accounted for during calculations if the overall oil yield numbers are desired. FIGS. 7 and 8 are presented for comparative purposes so the oil present in the thin stillage is not accounted for. The thin stillage that was not treated with Fuelzyme had 20 mL of emulsion/L (gray column), while the Fuelzyme treated thin stillage contained 15 mL of emulsion/L (horizontal-lined column). After pressing in the screw press, the press liquor without Fuelzyme increased in emulsion content up to 31.25 mL/L (vertical lined column), a 56.3% increase, although the standard deviation was large enough to encompass the initial thin stillage emulsion result. The Fuelzyme treated press liquor contained 22.5 mL (right diagonally-lined column) of emulsion/L for a 50.0% increase in emulsion, with very small standard deviations.

As illustrated by the present example, screw pressing reduced the solids oil content and increased the oil in the press liquor by an equal measure. Oil partitioned into the press liquor is available for separation and recovery.

Figure 9:
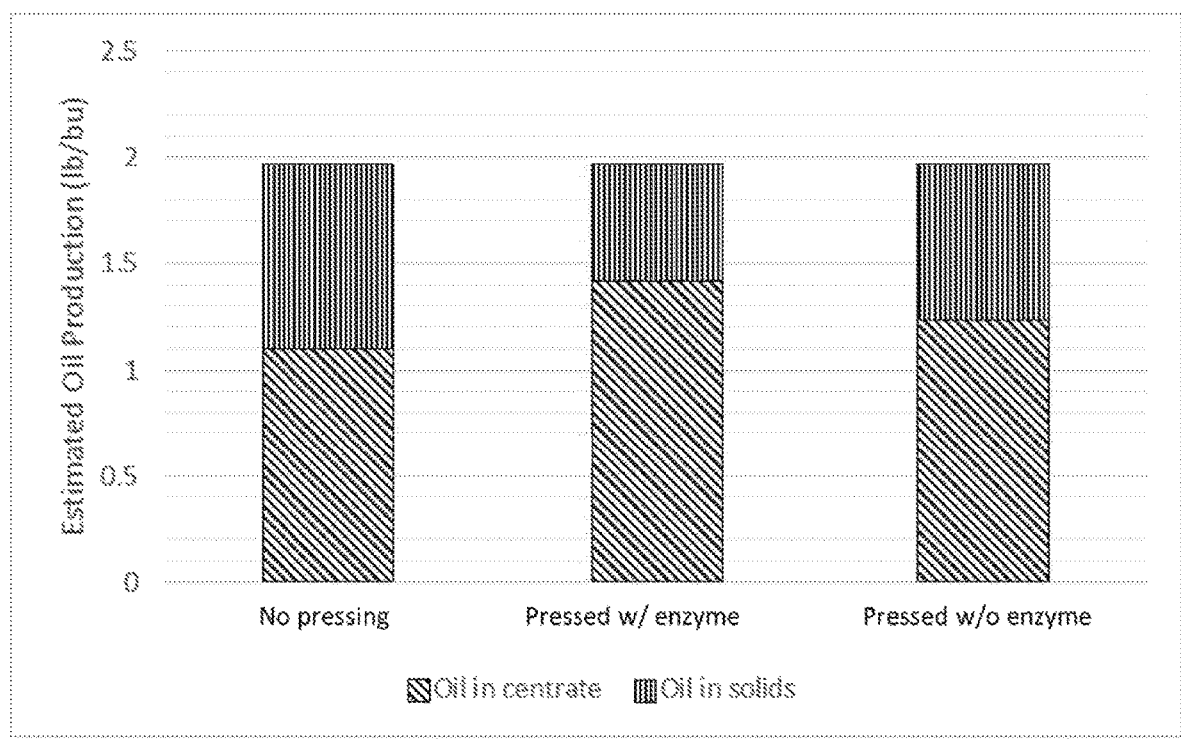
FIG. 9 is a graphical representation of distribution of oil content after decanter centrifuge with different oil liberation processes.
Figure 10:
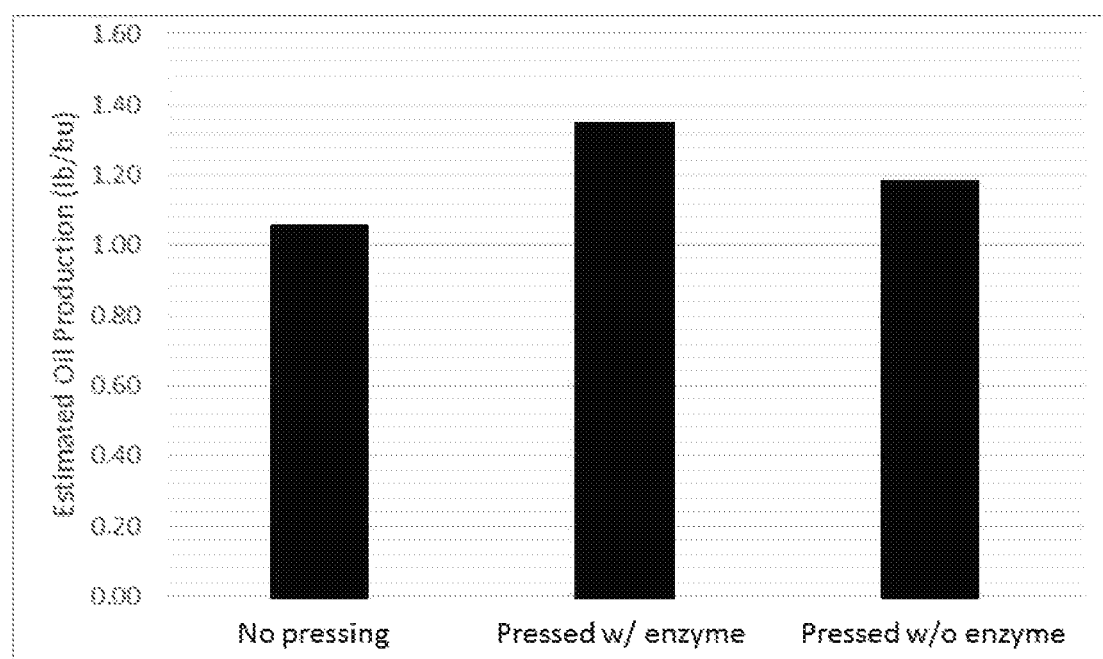
FIG. 10 is a graphical representation of estimated oil production from pressed wet cake with different oil liberation processes.

Also, it has been determined that corn contains enough oil to theoretically produce 1.97 lb/bu. It has also been determined that 1.05 lb/bu can be recovered from thin stillage operating at 95% efficiency, which means that 1.11 lb/bu of oil is present in the thin stillage. Accordingly, this means that 0.86 lb/bu of oil is theoretically present in the wet cake and available for recovery by techniques according to the present disclosure. FIG. 9 illustrates the changes in the oil content in the solids and liquid streams using extraction data from FIGS. 7 and 8. The liquid in FIG. 9 is a combination of the press liquor (except for the "no pressing" example) from the screw press and the thin stillage from the decanter that is not used for diluting. The liquid stream can be sent to downstream oil recovery processes. The "solids" refers to wet cake (without pressing and with pressing as indicated). As shown in FIG. 8, the oil content of the liquid stream is 1.11 lb/bu for the liquid stream that includes thin stillage only and does not include a press liquor ("no pressing"). By pressing wet cake in a screw press as described herein to recover a press liquor and combining the press liquor with the remaining thin stillage from the decanter to form the liquid stream, the oil content of the liquid stream increases to 1.42 lb/bu and 1.25 lb/bu with and without Fuelzyme, respectively. Assuming that a post-distillation oil system can recover 95% of the oil in the liquid stream, in this example, screw pressing wet cake from whole stillage treated with Fuelzyme would increase total oil production to 1.34 lb/bu. Without Fuelzyme treatment, in this example, oil production would increase to 1.18 lb/bu, as shown in FIG. 10.

Some additional non-limiting embodiments are provided below to further exemplify the present disclosure:

1. A method of extracting oil from a processed plant material, wherein the method comprises:
   (a) providing a slurry comprising:
      i) processed plant material; and
      ii) an aqueous carrier, wherein the slurry comprises a total solids content in a range from 15 to less than 35% (wt/wt) based on the total weight of the slurry;
   (b) applying pressure to the slurry to move oil from the processed plant material to the aqueous carrier;
   (c) separating the slurry into a liquid fraction and a solid fraction; and
   (c) recovering or separating oil from the liquid fraction.
2. The method of embodiment 1, wherein the slurry comprises a total solids content in a range from 15 to 30%, based on the total weight of the slurry.
3. The method of embodiment 1, wherein the slurry comprises a total solids content in a range from 17 to 25%, based on the total weight of the slurry.
4. The method of embodiment 1, wherein the slurry comprises a total solids content in a range from about 20% (wt/wt) based on the total weight of the slurry.
5. The method as in one of embodiments 1-4, wherein applying pressure and separating the slurry comprises mechanically pressing the processed plant material against a screen to separate the slurry into a liquid fraction and a solid fraction.
6. The method as in one of embodiments 1-5 wherein applying pressure and separating the slurry comprises mechanically passing the processed plant material through a screw press to separate the slurry into a liquid fraction and a solid fraction.
7. The method as in one of embodiments 1-6, wherein the average particle size of the slurry is reduced prior to applying pressure.
8. The method as in one of embodiments 1-7 further comprising applying a pressure above ambient pressure to the slurry to generate a second slurry, wherein the slurry comprises a first slurry.
9. The method of embodiment 8, wherein the applying pressure comprises applying pressure from about 200-600 psi.
10. The method as in one of embodiments 1-9, further comprising heating the slurry above ambient temperature to generate a second slurry, wherein the slurry comprises a first slurry.
11. The method of embodiment 10, wherein heating comprises heating from about 21° C. (70° F.) to about 100° C. (212° F.).

12. The method as in one of embodiments 8-11, further comprising applying pressure to the second slurry to generate a second liquid fraction and a second solid fraction.
13. The method as in one of embodiments 8-12, wherein the applying pressure to the second slurry comprises mechanically pressing the second slurry against a screen to separate the second slurry into a second liquid fraction and a second solid fraction.
14. The method of embodiment 8-13, wherein the applying pressure to the second slurry comprises mechanically passing the second slurry through a screw press to separate the second slurry into a second liquid fraction and a second solid fraction.
15. The method as in one of embodiments 1-14, further comprising, prior to step (c) combining the first liquid fraction, the second liquid fraction, and the second solid fraction to form a combined fraction.
16. The method of embodiment 15 further comprising distilling the combined fraction to separate alcohol and solids, and further processing the solids to a stillage composition.
17. The method as in one of embodiments 1-16, wherein the providing the first slurry comprises separating the processed plant material with a centrifuge, a gravity screen, and combinations thereof.
18. The method as in one of embodiments 1-17, wherein the processed plant material comprises milled grain.
19. The method as in one of embodiments 1-18, wherein the milled grain comprises dry-milled grain.
20. The method as in one of embodiments 18-19, wherein the milled grain comprises whole ground grain.
21. The method of embodiment 20 wherein the whole ground grain comprises corn.
22. The method as in one of embodiments 1-21, wherein the aqueous carrier comprises process water, thin stillage, ethanol, or combinations thereof.
23. The method as in one of embodiments 1-22, wherein the aqueous carrier comprises at least 50 percent water based on the total volume of the carrier.
24. The method as in one of embodiments 1-22, wherein the aqueous carrier comprises less than 10 percent water based on the total volume of the carrier.
25. The method as in one of embodiments 1-22, wherein the aqueous carrier comprises less than 5 percent water based on the total volume of the carrier.
26. The method as in one of embodiments 1-22, wherein the aqueous carrier comprises less than 1 percent water based on the total volume of the carrier.
27. The method as in one of embodiments 1-26, wherein the aqueous carrier comprises less than 0.5 percent organic solvent based on the total volume of the carrier.
28. The method as in one of embodiments 1-26, wherein the aqueous carrier does not include added exogenous (added) organic solvent.
29. The method as in one of embodiments 1-28, wherein the slurry is chosen from grain mash, fermentation beer, whole stillage, wet cake, and combinations thereof.
30. The method as in one of embodiments 1-29, wherein the slurry is chosen from a corn ethanol process that includes grinding, mashing, fermenting, and distilling.
31. The method as in one of embodiments 1-30, wherein the slurry is fermentation beer.
32. The method as in one of embodiments 1-30, wherein the slurry is whole stillage.
33. The method as in one of embodiments 1-30, wherein the slurry comprises wet cake.
34. The method of embodiment 33, wherein providing the wet cake comprises separating whole stillage into thin stillage and wet cake so that the wet cake comprises a total solids content in a range from 15 to less than 35% (wt/wt) based on the total weight of the wet cake.
35. The method as in one of embodiments 33, wherein providing the wet cake comprises:
    i) separating whole stillage into thin stillage and wet cake, wherein the wet cake comprises a total solids content of 35% or greater (wt/wt) based on the total weight of the wet cake; and
    ii) adding an aqueous carrier to the wet cake so that the wet cake comprises a total solids content in a range from 15 to less than 35% based on the total weight of the wet cake.
36. The method of embodiment 35, wherein the aqueous carrier comprises thin stillage.
37. The method as in one of embodiments 34-36, wherein separating whole stillage into thin stillage and wet cake comprises passing whole stillage through a separation apparatus.
38. The method of embodiment 37, wherein the separation apparatus is chosen from a centrifuge, a gravity screen, and combinations thereof.
39. The method as in one of embodiments 30-38, wherein the slurry comprises wet cake, wherein the wet cake in step (a) comprises corn oil in an amount of 10 percent (wt/wt) or less based on the total weight of the wet cake
40. The method of embodiment 39, wherein the corn oil comprises 8 percent (wt/wt) or less based on the total weight of the wet cake.
41. The method of embodiment 39, wherein the corn oil comprises 6 percent (wt/wt) or less based on the total weight of the wet cake.
42. The method of embodiment 39, wherein the corn oil comprises 4 percent (wt/wt) or less based on the total weight of the wet cake.
43. The method as in one of embodiments 1-42, further comprising prior to step (b), treating the processed plant material with one or more enzymes.
44. The method as in one of embodiments 1-43, further comprising prior to step (b), treating the slurry with one or more enzymes.
45. The method of embodiment 44 wherein treating the slurry comprises adding the one or more enzymes to whole stillage and/or wet cake.
46. The method as in one of embodiments 43-45, wherein the one or more enzymes is selected from amylase enzymes, one or more cellulase enzymes, one or more protease enzymes, and combinations thereof.
47. The method as in one of embodiments 1-46, further comprising applying additional shear to the first or second slurry via a mixer.
48. A system for extracting oil from a processed plant material, wherein the system comprises:
    a) a source of a slurry comprising:
       i) processed plant material; and
       ii) an aqueous carrier, wherein the slurry comprises a total solids content in a range from 15 to less than 35% (wt/wt) based on the total weight of the slurry;
    b) an oil liberation system in fluid communication with the source of the slurry, wherein the oil liberation system is configured to (adapted to) apply pressure to the slurry to force (transport, move) oil from the processed plant material to the aqueous carrier;

c) a solid liquid separation system configured to separate the slurry into a liquid fraction and a solid fraction; and d) an oil recovery or separation system in fluid communication with the solid liquid separation system to receive the liquid fraction, wherein the oil recovery or separation system is configured to recover or separate oil from the liquid fraction.

49. The system of embodiment 48, wherein the separation system is selected from a screw press, centrifuge, screens or combinations thereof.

50. The system as in one of embodiments 48-49, wherein the oil liberation system and solid liquid separation are combined.

51. The system of embodiment 50, wherein the combined systems comprises a screw press.

52. The system as in one of embodiments 48-51, further comprising a heat and pressure inducing system.

53. The system as in one of embodiments 48-52, further comprising a particle size reduction system in fluid communication with and located prior to the separation system.

54. A system as in one of embodiments 48-53 further comprising:

a source of one or more enzymes, the source of one or more enzymes in fluid communication with the separation system, wherein the source of one or more enzymes can be combined with the slurry to enzymatically treat the slurry prior to the slurry being separated into the liquid fraction and the solid fraction.

55. The system as in one of embodiments 48-54, wherein the slurry comprises total solids content in a range from 15 to 30% (wt/wt) based on the total weight of the slurry.

56. The system as in one of embodiments 48-54, wherein the slurry comprises total solids content in a range from 17 to 25% (wt/wt) based on the total weight of the slurry.

57. The system as in one of embodiments 48-57, wherein the slurry comprises total solids content in a range from about 20% (wt/wt) based on the total weight of the slurry.

58. The system as in one of embodiments 48-56, wherein the enzymes comprises one or more amylase enzymes, one or more cellulase enzymes, one or more protease enzymes, and combinations thereof.

59. A method of extracting oil from a processed plant material, wherein the method comprises:

(a) providing a slurry comprising:
 i) processed plant material; and
 ii) an aqueous carrier, wherein the slurry comprises a total solids content in a range from 15 to less than 35% (wt/wt) based on the total weight of the slurry, wherein providing the slurry comprises screening the processed plant material to separate the slurry into a first liquid fraction and a first solid fraction; and (b) pressing the first solid fraction to separate the first solid fraction into a second liquid fraction and a second solid fraction and to move oil into the second liquid fraction; and (c) recovering or separating oil from the second liquid fraction.

60. The method of embodiment 59 further comprising applying to the first solid fraction a pressure above ambient pressure or heating above an ambient temperature to generate a second slurry, wherein the slurry comprises a first slurry.

61. The method of embodiment 60, further comprising applying pressure to the second slurry to separate the second slurry to into a third liquid fraction and a third solid fraction; and recovering oil from the third liquid fraction.

Although the present disclosure provides references to embodiments, persons skilled in the art will recognize that changes may be made to the order of events or steps, form, and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

What is claimed is:

1. A method of extracting oil from a grain in a biochemical process, comprising:

(a) grinding grain to reduce a size of the grain to form ground grain;

(b) fermenting the ground grain to produce beer;

(c) distilling the beer to recover a biochemical from the beer and to form whole stillage;

(d) separating at least a portion of at least one of the beer, the whole stillage, or a combination thereof into a first liquid fraction and a first solids fraction, wherein the first solids fraction comprises, or is adjusted to comprise, a total solids content in a range from 15 to less than 35% (wt/wt) based on the total weight of the first solids fraction and after step (d);

(e) applying pressure to the first solids fraction to separate the first solids fraction into a second liquid fraction and a second solids fraction and to transfer oil into the second liquid fraction; and (f) recovering or separating oil from the second liquid fraction.

2. The method of claim 1, wherein applying pressure comprises mechanically pressing the first solids fraction against a screen to separate the first solids fraction into the second liquid fraction and the second solids fraction.

3. The method of claim 1, wherein applying pressure comprises passing the first solids fraction through a screw press to separate the first solids fraction into the second liquid fraction and the second solids fraction.

4. The method of claim 1, wherein the applying pressure to the first solids fraction comprises applying pressure from about 200-600 psi.

5. The method of claim 1, further comprising heating the first solids fraction from about 21° C. (70° F.) to about 100° C. (212° F.).

6. The method of claim 1, further comprising prior to step (d) treating the whole stillage fraction with one or more enzymes or prior to step (e), treating the first solids fraction with one or more enzymes.

7. The method of claim 6, wherein the one or more enzymes are selected from amylase enzymes, one or more cellulase enzymes, one or more protease enzymes, and combinations thereof.

8. The method of claim 1, wherein the first solids fraction is obtained from ground corn ethanol process.

9. The method of claim 1, further comprising adding an aqueous carrier to the first solids fraction to adjust the first solids fraction and provide a the first solids fraction with the total solids content in a range from 15 to less than 35% (wt/wt) based on the total weight of the first solids fraction.

10. The method of claim 9, wherein the aqueous carrier comprises thin stillage, ethanol, or combinations thereof.

11. The method of claim 1, further comprising:
(a) adding an aqueous carrier to the second solids fraction to adjust the second solids fraction and provide the second solids fraction with a total solids content in a range from 15 to less than 35% (wt/wt) based on the total weight of the second solids fraction;
(b) applying pressure to the second solids fraction to separate the second solids fraction into a third liquid fraction and a third solids fraction and to transfer oil into the third liquid fraction and to transfer oil into the third liquid fraction; and
(c) recovering or separating oil from the third liquid fraction.

12. The method of claim 11, wherein applying pressure comprises passing the first solids fraction through a first screw press and passing the second solids fraction through a second screw press.

13. The method of claim 1, wherein separating at least a portion of at least one of the beer, the whole stillage or combination thereof into the first liquid fraction and the first solids fraction comprises processing at least a portion of at least one of the beer, the whole stillage or combination thereof with a decanter centrifuge, the decanter centrifuge being operated to provide the first solids fraction having the total solids content in a range from 15 to less than 35% (wt/wt) based on the total weight of the first solids fraction.

14. The method of claim 1, wherein separating at least a portion of at least one of the beer, the whole stillage or combination thereof into the first liquid fraction and the first solids fraction comprises processing at least a portion of at least one of the beer, the whole stillage or combination with a gravity screen and wherein applying pressure comprises passing the first solids fraction through a screw press to separate the first solids fraction into the second liquid fraction and the second solids fraction.

15. The method of claim 14, further comprising, prior to passing the first solids fraction through a screw press:
(a) adding an aqueous carrier to the first solids fraction to adjust the first solids fraction and provide the first solids fraction with the total solids content in a range from 15 to less than 35% (wt/wt) based on the total weight of the first solids fraction; and
(b) heating the first solids fraction from about 21° C. (70° F.) to about 100° C. (212° F.).

16. The method of claim 1, further comprising reducing the particle size of the beer or the whole stillage or both prior to step (d) or reducing the first solids fraction prior to step (e).

17. A method of extracting oil from a grain in a biochemical process, comprising:
(a) grinding grain to reduce a size of the grain to form ground grain;
(b) fermenting the ground grain to produce beer;
(c) distilling the beer to recover a biochemical from the beer and to form whole stillage;
(d) separating at least a portion of at least one of the beer or the whole stillage into a first liquid fraction and a first solids fraction, wherein the first solids fraction comprises, or is adjusted to comprise, a total solids content in a range from 15 to less than 35% (wt/wt) based on the total weight of the first solids fraction and after step (d);
(e) applying pressure to the first solids fraction to separate the first solids fraction into a second liquid fraction and a second solids fraction;
(f) adding a diluent to reduce the solids content of the second solids fraction to produce a diluted second solids fraction;
(g) heating the diluted second solids fraction to produce a heated and diluted second solids fraction;
(h) applying pressure to the heated and diluted second solids fraction to separate the heated and diluted second solids fraction into a third liquid fraction and a third solids fraction and to transfer oil into the third liquid fraction; and
(i) recovering or separating oil from the third liquid fraction.

18. The method of claim 1, wherein separating at least a portion of at least one of the beer, the whole stillage, or a combination thereof into a first liquid fraction and a first solids fraction comprises, prior to distillation, separating at least a portion of the beer into a first liquid fraction and a first solids fraction.

19. The method of claim 1, wherein separating at least a portion of at least one of the beer, the whole stillage, or a combination thereof into a first liquid fraction and a first solids fraction comprises, after distillation, separating at least a portion of the whole stillage into a first liquid fraction and a first solids fraction, wherein the first liquid fraction is thin stillage, and wherein applying pressure comprises passing the first solids fraction through a screw press to separate the first solids fraction into the second liquid fraction and the second solids fraction.

20. The method of claim 1, wherein the first solids fraction comprises a total solids content in a range from 20 to less than 35% (wt/wt) based on the total weight of the first solids fraction and after step (d).

21. The method of claim 17, wherein the diluent is chosen from fresh water, alcohol, thin stillage, process water, and combinations thereof.

22. The method of claim 17, wherein heating the diluted second solids fraction to produce a heated and diluted second solids fraction comprises exposing the diluted second solids to a temperature in a range from 65.5° C. (150° F.) to 100° C. (212° F.); and further comprising exposing the diluted second solids fraction to a pressure in a range from 20 to 600 psi.

* * * * *

UNITED STATES PATENT AND TRADEMARK OFFICE
CERTIFICATE OF CORRECTION

PATENT NO. : 11,345,875 B2
APPLICATION NO. : 16/776295
DATED : May 31, 2022
INVENTOR(S) : Blake A. Schnell et al.

It is certified that error appears in the above-identified patent and that said Letters Patent is hereby corrected as shown below:

In the Claims

Claim 9, Column 16, Line 65, "solids fraction and provide a the first solids fraction with the" should be – solids fraction and provide the first solids fraction with the –

Signed and Sealed this
Sixteenth Day of August, 2022

Katherine Kelly Vidal
Director of the United States Patent and Trademark Office